United States Patent [19]

Curtis et al.

[11] Patent Number: 4,528,182

[45] Date of Patent: Jul. 9, 1985

[54] STABLE ANTIPLAQUE DENTIFRICE WITH IMPROVED FOAMING

[75] Inventors: John P. Curtis, Glen Gardner; Richard J. Crawford, Asbury; Kathleen M. Yuhasz, Fords, all of N.J.

[73] Assignee: Colgate-Palmolive Company, New York, N.Y.

[21] Appl. No.: 513,473

[22] Filed: Jul. 13, 1983

[51] Int. Cl.³ .......................... A61K 7/16; A61K 7/22
[52] U.S. Cl. .......................................... 424/54; 424/49
[58] Field of Search ....................................... 424/49–58

[56] References Cited

U.S. PATENT DOCUMENTS

| | | | |
|---|---|---|---|
| 3,927,201 | 12/1975 | Baines et al. | 424/54 |
| 3,937,805 | 2/1976 | Harrison | 424/54 |
| 3,957,967 | 5/1976 | L'Orange | 424/54 |
| 3,988,435 | 10/1976 | Humbert et al. | 424/54 |
| 4,025,616 | 5/1977 | Haefele | 424/54 |
| 4,029,759 | 6/1977 | Humbert et al. | 424/49 |
| 4,036,950 | 7/1977 | Baines et al. | 424/54 |
| 4,059,624 | 11/1977 | Harrison | 424/54 |
| 4,067,962 | 1/1978 | Juneja | 424/54 |
| 4,088,752 | 5/1978 | Muhlemann et al. | 424/52 |
| 4,098,878 | 7/1978 | Baines et al. | 424/49 |
| 4,117,107 | 9/1978 | Shapiro et al. | 424/54 |
| 4,117,108 | 9/1978 | Shapiro et al. | 424/54 |
| 4,122,162 | 10/1978 | Muhlemann et al. | 424/49 |
| 4,123,517 | 10/1978 | Baines et al. | 424/54 |
| 4,130,637 | 12/1978 | Bauman | 424/54 |
| 4,181,621 | 1/1980 | Raaf et al. | 424/54 |
| 4,198,392 | 4/1980 | Juneja | 424/54 |
| 4,219,541 | 8/1980 | Schmid et al. | 424/54 |
| 4,282,204 | 8/1981 | Phillips et al. | 424/49 |
| 4,301,141 | 11/1981 | Scheller | 424/49 |
| 4,308,253 | 12/1981 | Schmid et al. | 424/54 |
| 4,332,791 | 6/1982 | Raaf et al. | 424/54 |
| 4,339,429 | 7/1982 | Raaf et al. | 424/54 |
| 4,343,786 | 8/1982 | Baines et al. | 424/52 |
| 4,346,072 | 8/1982 | Baines et al. | 424/49 |
| 4,363,795 | 12/1982 | Wahlstam | 424/54 |

*Primary Examiner*—Shep K. Rose
*Attorney, Agent, or Firm*—Robert L. Stone; Murray M. Grill; Herbert S. Sylvester

[57] ABSTRACT

A stable antiplaque dentifrice with improved foaming containing an antiplaque quaternary ammonium compound, a betaine surfactant to improve foaming without inactivating the antibacterial and antiplaque activity of the quaternary ammonium compound, a humectant selected from the group consisting of polyethylene glycol, sorbitol and mixtures thereof, and a nonionic gelling agent, preferably hydroxyethylcellulose, in an aqueous vehicle containing a dental abrasive. A fluorine-containing compound such as monofluorophosphate is an optionally preferred ingredient.

14 Claims, No Drawings

STABLE ANTIPLAQUE DENTIFRICE WITH IMPROVED FOAMING

BACKGROUND AND PRIOR ART

This patent application is a companion to patent application Ser. No. 513,474, filed of even date and having a common assignee, which issued as U.S. Pat. No. 4,490,353 on Dec. 25, 1984.

The present invention relates to an antiplaque dentifrice containing a quaternary active ingredient and at least 1.5% and up to 2% betaine surfactant by weight, such as cocoamidopropylbetaine, lauramidopropylbetaine, cocobetaine, etc., which enhances foaming and does not inactivate the antibacterial activity of the quaternary compound. Nonionic surfactants fail to afford sufficient foaming, and anionic surfactants inactivate the quaternary antibacterial activity. Carbowax 600 (polyethylene glycol) and/or sorbitol replace propylene glycol and glycerin as humectant in order to afford stability to the betaine-containing composition. Also, carboxymethyl cellulose is preferably avoided because large organic molecules deactivate the quaternary compound. Nonionic gums such as hydroxyethylcellulose is used as gelling/thickening agent for the dental cream. More specifically, this composition is free of anionic and nonionic surfactants and glycerin; and contains only sorbitol and/or polyethylene glycol humectant.

It has been found that the addition of a betaine surfactant to an antiplaque dental formulation based on quaternary active ingredients, improves the foaming characteristics thereof, without deactivating the quaternary antimicrobial activity. It has additionally been found that humectants other than glycerin is required in the betaine system to effect cosmetic stability, specifically polyethylene glycol and/or sorbitol. The limitation of the gelling/thickening agent to nonionic gums such as hydroxyethylcellulose is also a necessary expedient.

The ability of quaternary ammonium compounds to inhibit the formation of dental plaque is well documented. These compounds, however, present a problem when formulated in a dentifrice in that they are deactivated by traditional anionic surfactants such as sodium lauryl sulfate. Stable, clinically effective dental formulations have been made with quaternary ammonium compounds and nonionic surfactants, but these formulations are very poor foamers and result in inferior products. Compositions containing antiplaque quaternary ammonium compounds and nonionic surfactants are disclosed in U.S. Pat. Nos. 4,080,441, 4,110,429, 4,118,472, 4,118,473, 4,118,475, 4,118,476, and British Pat. No. 1,573,356.

U.S. Pat. No. 4,161,518 discloses a dentifrice composition for inhibiting plaque formation containing 0.05–1% by weight of a quaternary ammonium organosiloxane as the active antibacterial agent in a suitable vehicle containing suitable polishing agents, fluoride compounds, anionic surfactants, flavoring and sweetening agents, thickening agents such as carboxymethylcellulose, humectants such as glycerin, sorbitol and other polyhydric alcohols.

U.S. Pat. No. 3,988,435 discloses pharmaceutical compositions including a dentifrice containing a quaternary ammonium dihydrochalcone glucoside as the antibacterial agent having a sweet taste, as well as abrasives, surfactants including nonionics and "derivatives of fatty amines with betaine structures," swelling, gelling or thickening agents such as hydroxyalkylcellulose particularly hydroxyethylcellulose, polyethylene glycols, polypropylene glycols, etc., humectants such as sorbitol, mannitol, glycerin, propylene glycol, colorants, and flavors.

All of aforesaid cited patents simply list the conventional additives useful in dentifrice compositions. There is no disclosure of the use of the betaine as the exclusive surfactant in the production of a high foaming dentifrice. There is also no disclosure nor recognition of the necessity to limit the humectant to polyethylene glycol and/or sorbitol, and the thickening agent to nonionic gums such as hydroxyethylcellulose, in order to obtain a cosmetically stable dentifrice in a betaine-quat system.

U.S. Pat. No. 4,363,795 and its counterpart International Patent Publication No. WO 80/00057 to Wahlstam disclose a cleaning agent for dentine surfaces containing a quaternary ammonium compound, an ampholytic tenside which may be an imidazoline or a betaine and a sequestering agent of the aminocarboxylic acid type which has a synergistic effect as to the antibacterial properties of the treating solution. All the examples are in the form of cleaning solutions. There is no mention of dental creams, nor the use of humectants and thickening agents.

U.S. Pat. No. 4,130,637 discloses a specific group of betaine compounds, or a mixture of said betaine and its corresponding carboxylic acid quaternary ammonium salt in a 9:1 ratio, as non-staining antimicrobial antiplaque agents in a dentifrice vehicle containing the aforelisted conventional humectants and gelling agents, and a nonionic surfactant. This patent fails to disclose the necessity of using a betaine surfactant exclusively, the specific nonionic gelling agent hydroxyethylcellulose and the specific humectant polyethylene glycol and/or sorbitol, in order to obtain a stable, high foaming quaternary-containing antiplaque dentifrice.

U.S. Pat. Nos. 4,117,107 and 4,117,108 also disclose a specific group of betaine compounds and their salts as antiplaque agents in a dentifrice vehicle containing the conventional humectants and gelling agents, as well as anionic/nonionic surfactants. There is no disclosure of an antibacterial quaternary ammonium compound, and a betaine surfactant exclusively. There is also no recognition of the specificity of humectant and gelling agent and the exclusion of anionic/nonionic surfactants in a quaternary-betaine system, which is necessary in order to obtain a stable high foaming antiplaque dentifrice.

However, none of the above cited prior art discloses a cosmetically stable antiplaque dentifrice with improved foaming containing as the essential ingredients a cationic quaternary ammonium antiplaque compound, a zwitterionic betaine surfactant, a humectant compatible with the cationic antiplaque agent selected from the group consisting of polyethylene glycol and sorbitol, and the nonionic gelling agent hydroxyethylcellulose, in an aqueous vehicle containing a dental abrasive.

SUMMARY OF THE INVENTION

It has now been found that dental cream formulations containing antiplaque quaternary ammonium compounds may be stabilized and provide better foaming when betaine type surfactants replace the traditional anionic and nonionic surfactants. Humectants such as polyethylene glycol and sorbitol must replace the conventional glycerin for better cosmetic stability of the product. Nonionic gums such as hydroxyethylcellulose replace the anionic carboxymethylcellulose gelling agent which also has the potential to deactivate the quaternary compound.

Accordingly, a primary object of the present invention is to provide a better foaming antiplaque dentifrice based on quaternary active ingredients by the incorporation of a zwitterionic betaine surfactant as the foaming agent.

Another object of the present invention is to provide a cosmetically stable foaming antiplaque dentifrice containing polyethylene glycol and/or sorbitol as humectant which is compatible with the betaine and the quaternary active ingredients.

Still another object of this invention is to provide a stable foaming antiplaque dentifrice containing the nonionic gum, hydroxyethylcellulose, as gelling agent to stabilize the betaine-quat system and to prevent deactivation of the quaternary active ingredient by the large organic molecules of carboxymethylcellulose.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the present invention, as embodied and broadly described herein, the novel stable foaming antiplaque dentifrice of this invention comprises a quaternary ammonium antiplaque compound, a zwitterionic betaine surfactant, a humectant selected from the group consisting of polyethylene glycol, sorbitol and mixtures thereof, a nonionic gelling agent such as hydroxyethylcellulose in an aqueous vehicle containing a dental abrasive.

More specifically, present invention relates to a stable antiplaque dentifrice formulation with improved foaming, comprising an effective antimicrobial amount of a quaternary ammonium compound, about 1.5-2% by weight betaine, about 20-30% by weight humectant selected from the group consisting of polyethylene glycol, sorbitol and mixtures thereof, and about 0.5-2% hydroxyethylcellulose, in an aqueous vehicle containing about 40-60% water-insoluble dental abrasive.

Cationic antibacterial materials are well known in the art. See, for instance the section on "Quaternary Ammonium and Related Compounds" in the article on "Antiseptics and Disinfectants" in Kirk-Othmer Encyclopedia of Chemical Technology, 2nd edition (Vol. 2, pp. 632-635), incorporated herein by reference. Cationic materials which possess antibacterial activity (i.e. are germicides) are used against bacteria and have been used in oral compositions to counter plaque formation caused by bacteria in the oral cavity.

Among the most common of these antibacterial antiplaque quaternary ammonium compounds is benzethonium chloride, also known as Hyamine 1622 or diisobutylphenoxyethoxyethyl dimethyl benzyl ammonium chloride, and cetyl pyridinium chloride. In an oral preparation this material is highly effective in promoting oral hygiene by reducing formation of dental plaque and calculus, which is generally accompanied by a reduction in periodontal diseases. Other cationic antibacterial agents of this type are those mentioned, for instance, in U.S. Pat. Nos. 2,984,639, 3,325,402, 3,431,208 and 3,703,583, and British Pat. No. 1,319,396.

Other antibacterial antiplaque quaternary ammonium compounds include those in which one or two of the substituents on the quaternary nitrogen has a carbon chain length (typically alkyl group) of some 8 to 20, typically 10 to 18, carbon atoms while the remaining substituents have a lower number of carbon atoms (typically alkyl or benzyl group), such as 1 to 7 carbon atoms, typically methyl or ethyl groups. Dodecyl trimethyl ammonium bromide, benzyl dimethyl stearyl ammonium chloride, cetyl pyridinium chloride and quaternized 5-amino-1,3-bis(2-ethylhexyl)-5-methyl hexa hydro-pyrimidine are typical quaternary ammonium antibacterial agents.

The dentifrice formulation of present invention contains an effective amount of the antiplaque quaternary ammonium compound, preferably about 0.01-5%, and most preferably 0.025-1% by weight of the composition.

The ability of quaternary ammonium compounds to inhibit the formation of dental plaque is well known. However, they are deactivated by the anionic surfactants such as sodium lauryl sulfate conventionally used in dentifrice formulations. The substitution of nonionic surfactants for the anionic surfactants eliminates the deactivation problem but results in products with poor foaming.

The incorporation of betaine surfactants into antiplaque dental formulations based on quaternary active ingredients unexpectedly improves the foaming of these formulations without deactivating the quaternary.

The betaine component of present dentifrice composition has the general formula:

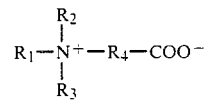

wherein $R_1$ is an alkyl group having 10 to about 20 carbon atoms, preferably 12 to 16 carbon atoms or the amido radical:

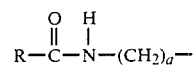

wherein R is an alkyl group having about 10 to 20 carbon atoms and a is the integer 1 to 3; $R_2$ and $R_3$ are each alkyl groups having 1 to 3 carbons and preferably 1 carbon; $R_4$ is an alkylene or hydroxyalkylene group having from 1 to 4 carbon atoms and, optionally, one hydroxyl group. Typical alkyldimethyl betaines include decyl betaine or 2-(N-decyl-N,N-dimethylammonio)acetate, coco betaine or 2-(N-coco-N,N-dimethylammonio)acetate, myristyl betaine, palmityl betaine, lauryl betaine, cetyl betaine, stearyl betaine, etc. The amidobetaines similarly include cocoamidoethyl betaine, cocoamidopropyl betaine, lauramidopropyl betaine and the like.

The betaines, which are zwitterionic materials, function as a foaming agent in the quaternary-containing dentifrice compositions. They act cationically over a wide pH range, but do not deactivate the quaternary antimicrobial activity. This is shown by in vitro tests using wool swatches, which simulate human skin and oral tissue, as the absorptive material in the Red 80 Stain test, J. Soc. Cosmet, Chem. 31, 271-278 (Sept., Oct. 1980). Wool has the same type of absorptive properties as oral tissue due to similar isoelectric and isoionic points.

Using the Red 80 Dye Test, the following experiment illustrates that the betaine surfactant doesn't deactivate the quaternary. The Red 80 Stain Test was performed using a solution of cocoamidopropyl betaine alone, benzethonium chloride alone, and a mixture of cocoamidopropylbetaine and benzethonium chloride. The degree of staining of the wool swatches treated with benzethonium chloride alone and the mixture of benzethonium chloride and betaine was nearly equal, and both were stained darker than the cocoamidopropyl betaine treated swatch. This indicates that benzethonium chloride is a "stronger" cationic compound than the betaine i.e. it has a greater attraction to the wool than the betaine, indicating that the betaine doesn't deactivate the benzethonium chloride.

However, wool swatches treated with a mixture of benzethonium chloride and the anionic surfactant, sodium lauryl sulfate, exhibits no staining (no red color retention) indicating complete deactivation of the benzethonium chloride by the anionic surfactant.

The degree of staining of the wool swatches treated with a mixture of benzethonium chloride and the nonionic surfactant, polyoxyethylene (20 moles ethylene oxide) sorbitan di-iso stearate, was substantially equal to that of the benzethonium chloride alone. This indicates that the benzethonium is not deactivated by the nonionic surfactant.

In addition to the non-interference exhibited by the betaines with the quaternary activity, laboratory foam tests have shown that formulations containing both the quat and the betaine, foam 2-3 times better than the nonionic/quat formulations. The foam index for nonionic/quat compositions is about 20, whereas the foam index for betaine/quat compositions is about 40-60. The foam test used herein comprises placing 1 gram of the test dentifrice in 10 ml of 175 PPM water at 90° F. in a 100 ml graduated cylinder, shaking for 15 seconds and reading the foam height.

The zwitterionic betaines are completely compatible with the quaternary antimicrobial antiplaque agents, and impart detersive and improved foaming properties to the quaternary-containing dentifrice composition without deactivating the antimicrobial properties thereof. The amount of betaine effective in the production of improved foaming may be varied from about 1.5-2% active ingredient by weight of the total formulation. Greater amounts of betaine adversely affect the taste of the dentifrice.

Cosmetic problems of stability is incurred with all zwitterionic-containing dentifrices, such as crimp leakage of flavor. The flavor oozes and is not solubilized in the zwitterionic surfactant.

Accordingly, in order to effect cosmetic (physical) stability of the betaine system, a specific group of humectants which includes polyethylene glycol, sorbitol or mixtures thereof must be used. Glycerin and propylene glycol provide insufficient cosmetic stability to the betaine system. The polyethylene glycol and/or sorbitol may be used in amounts of about 20-30% by weight and preferably 20-25%.

Another essential ingredient in the present dentifrice is a gelling agent which is a nonionic gum, in an amount up to 5% by weight and preferably about 0.5-2%. It has been found that large organic anionic molecules such as carboxymethylcellulose have the potential to deactivate the quaternary antibacterial activity. Accordingly, hydroxyethylcellulose, which is a nonionic small organic molecule, effects a stable pituitous gel in the betaine-quat system of present invention, and is the preferred gelling agent. Other nonionic gelling agents may be used such as hydroxymethylcellulose, and the like.

It has been found that only by utilizing the specific combination of ingredients of betaine, humectant and gelling agent, can a stable antiplaque dentifrice with improved foaming based on the quaternary antibacterial compounds, be obtained.

The dentifrice of this invention, which is a toothpaste or dental cream, contains conventional water-insoluble polishing materials or dental abrasives, in amounts from about 20-75% and preferably about 40-60% by weight of the total formulation. Suitable examples of dental abrasives or polishing materials include sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, alumina, hydrated alumina, aluminum silicate, zirconium silicates, silica, bentonite, and mixtures thereof.

The dentifrice of this invention may also contain conventional additional ingredients such as coloring or whitening agents, preservatives, flavoring or sweetening materials, ammoniated materials such as monoammonium glycyrrhizinate, and preferably compounds which provide fluorine-containing ions such as sodium fluoride, stannous fluoride and sodium monofluorophosphate. These additional ingredients may each be added to the dentifrice in minimal amounts of up to 5% by weight, and preferably up to 1%, provided they do not interfere with the foaming, antiplaque and stability properties of the finished product.

The dentifrice of this invention is prepared by conventional methods of making toothpaste and/or dental creams. More specifically, a toothpaste may be prepared by forming a gel with hydroxyethylcellulose and water, adding thereto with mixing the powdered materials and humectant, followed by the addition with mixing of polishing agent and then the betaine and flavor, and tubing the final mixture.

In the practice of this invention to promote oral hygiene, the dentifrice according to this invention is applied regularly to dental enamel by brushing the teeth for 30-90 seconds at least once daily.

DETAILED DESCRIPTION OF THE INVENTION

The following examples are further illustrative of the nature of the present invention, but it is understood that the invention is not limited thereto. The compositions are prepared in the usual manner and all amounts and proportions referred to herein and in the appended claims are by weight unless otherwise indicated.

| Ingredients | % |
| --- | --- |
| Hydroxyethylcellulose | 1.0 |
| Carbowax 600[1] | 20.0 |
| Na Saccharin | 0.2 |
| MFP[2] | 0.76 |
| CAB[3] (35% A.I.) | 3.5 |
| Dicalcium Phosphate | 49.0 |
| BZCl[4] | 0.5 |
| D.I. H$_2$O | 24.04 |

| Ingredients | % |
| --- | --- |
| Flavor | 1.0 |

[1] Polyethylene glycol, mol. weight 600
[2] Sodium monofluorophosphate
[3] Cocoamidopropyl betaine
[4] Benzethonium chloride The hydroxyethylcellulose and water are premixed for 10 minutes to form a gel. The powdered materials MFP, BZCl and saccharin, and the Carbowax humectant is added to the gel and mixed for 10 to 20 minutes. The gelled mixture is added to dicalcium phosphate and mixed for 20 minutes at speed 8 in the Ross agitator. The betaine and flavor is added to the mixture and mixed for 5 minutes at speed 6 in the Ross agitator. The resultant dental cream which is cosmetically attractive is tubed.

Aging tests performed on this product in lined tubes at room temperature, 40° F. and 100° F. for 9 weeks, and in unlined tubes at 120° F. for 9 weeks, exhibit excellent cosmetic stability.

EXAMPLE 2

| Ingredients | % |
| --- | --- |
| Hydroxyethylcellulose | 1.1 |
| Carbowax 600 | 20.0 |
| Na Saccharin | 0.2 |
| MFP | 0.76 |
| CAB (35% A.I.) | 5.7 |
| Dicalcium Phosphate | 46.8 |
| BZCl | 0.5 |
| $H_2O$ | 24.04 |
| Flavor | 1.0 |

This dental cream is prepared in accordance with the procedure of Example 1. This product has a pH of 6.7 and a foam height of 55, but does not taste good.

EXAMPLE 3

| Ingredients | % |
| --- | --- |
| Hi Sweet peppermint | 1.0 |
| MAG[1] | 0.1 |
| BZCl | 0.5 |
| MFP | 0.76 |
| Na Saccharin | 0.2 |
| $H_2O$ | 23.44 |
| PEG 600[2] | 20.0 |
| Natrosol[3] | 1.0 |
| Dicalcium phosphate | 49.0 |
| CAB (30% A.I.) | 4.0 |

[1] Monoammonium glycyrrhizinate
[2] Polyethylene glycol, molecular weight 600
[3] Hydroxyethylcellulose This dental cream is prepared according to the procedure of Example 1, except that the pH is adjusted to 8.5 with dilute NaOH for hydration purposes, after the polyethylene glycol is added to the gelled premix.

The resultant cream looks good, has a foam height of 38–40, and shows excellent stability using aging tests over a period of 12 weeks at 100° F. as well as at 140° F. in unlined tubes for 3 weeks.

EXAMPLE 4

Example 3 is repeated except that glycerin replaces the polyethylene glycol humectant. This product gives a foam height of 46, but shows trace separation in 3 days at 140° F. and a wetness and separation at the neck of the tube at 120° F. in 3 weeks. This product is cosmetically unstable.

EXAMPLE 5

| Ingredients | % |
| --- | --- |
| $H_2O$ | 21.14 |
| Natrosol | 1.3 |
| Propylene glycol | 20.0 |
| Na Saccharin | 0.2 |
| BZCl | 0.5 |
| MAG | 0.1 |
| MFP | 0.76 |
| Dicalcium phosphate | 50.0 |
| CAB (30% A.I.) | 5.0 |
| Flavor | 1.0 |

This dental cream is prepared according to the procedure of Example 1 except that the propylene glycol humectant is mixed with the premix gel for only 10 minutes. The resulting product is good in appearance and foaming with a foam height of 44. However, it's instability is clearly evident by separation, wetness along the ribbon and clip leakage in 3 weeks at 8° F. and 40° F., and slight yellowing at 110° F. and 120° F. within 3 weeks.

EXAMPLE 6

| Ingredients | % |
| --- | --- |
| $H_2O$ | 19.68 |
| Natrosol | 1.1 |
| Carbowax 600 | 20.0 |
| Na Saccharin | 0.2 |
| BZCl | 0.5 |
| MAG | 0.1 |
| MFP | 0.76 |
| Dicalcium phosphate | 50.0 |
| CAB (30% A.I.) | 6.66 |
| Flavor | 1.0 |

This dental cream is prepared according to the procedure of Example 1.

The resulting product is slightly thick but exhibits good foaming and stability.

EXAMPLE 7

| Ingredients | % |
| --- | --- |
| $H_2O$ | 21.34 |
| Natrosol | 1.1 |
| Carbowax 600 | 20.0 |
| Na Saccharin | 0.2 |
| BZCl | 0.5 |
| MAG | 0.1 |
| MFP | 0.76 |
| $Ca_2P_2O_7$[1] | 50.0 |
| CAB (30% A.I.) | 5.0 |
| Flavor | 1.0 |

[1] Calcium pyrophosphate

This dental cream is prepared according to the procedure of Example 1.

The resulting cream is thick and grainy, which may be due to the coarseness of the calcium pyrophosphate dental abrasive.

EXAMPLE 8

| Ingredients | % |
| --- | --- |
| H₂O | 17.68 |
| Natrosol | 1.1 |
| Carbowax 600 | 20.0 |
| Na Saccharin | 0.2 |
| BZCl | 0.5 |
| MAG | 0.1 |
| MFP | 0.76 |
| Dicalcium phosphate dihydrate | 42.0 |
| Anhydrous Dicalcium phosphate | 10.0 |
| CAB (30% A.I.) | 6.66 |
| Flavor | 1.0 |

EXAMPLE 9

| Ingredients | % |
| --- | --- |
| Carbowax 600 | 20.0 |
| Natrosol | 1.1 |
| Na Saccharin | 0.2 |
| MAG | 0.1 |
| BZCl | 0.5 |
| H₂O | 17.68 |
| MFP | 0.76 |
| Hydrated Alumina | 42.0 |
| Calcined Alumina | 10.0 |
| Cocoamidopropyl betaine (30% A.I.) | 6.66 |
| Flavor | 1.0 |
| pH | 8.3 |

This product shows complete stability after aging for 9 weeks at room temperature, 40° F., 100° F. and 120° F.

EXAMPLES 10 AND 11

| Ingredients | Ex. 10 % | Ex. 11 % |
| --- | --- | --- |
| PEG 600 | 20.0 | 20.0 |
| Natrosol | 1.1 | 1.3 |
| Na Saccharin | 0.3 | 0.3 |
| Hydrated Alumina | 42.0 | 42.0 |
| Calcined Alumina | 10.0 | 10.0 |
| Cocoamidopropyldimethyl betaine (30% A.I.) | 5.0 | 5.0 |
| MFP | 0.76 | 0.76 |
| Flavor | 1.0 | 1.0 |
| H₂O D.I. | 19.27 | 18.64 |
| BZCl | 0.5 | 0.5 |
| Red 40 (1% solution) | 0.07 | 0.07 |

EXAMPLE 12

| Ingredients | % |
| --- | --- |
| Sorbitol 70% | 28.0 |
| Natrosol | 1.1 |
| Na Saccharin | 0.3 |
| BZCl | 0.5 |
| MFP | 0.76 |
| Alumina | 42.0 |
| Calcined Alumina | 10.0 |
| Cocoamidopropyldimethyl betaine (30% A.I.) | 5.0 |
| Flavor | 1.0 |
| H₂O | 11.34 |
| Initial pH 7.4 | |
| 3 weeks pH 7.5 | |
| 6 weeks pH 7.6 | |

This product exhibits complete stability at 8° F. and 40° F. for a period of 9 weeks but slight wet cap at 110° F. and 120° F. after 3–9 weeks. In addition to the good physical stability of this product, the active ingredient content (ionic fluoride and the benzethonium chloride) remains stable as evidenced by the substantially stable pH.

EXAMPLE 13

| Ingredients | % |
| --- | --- |
| H₂O | 21.14 |
| Natrosol | 1.3 |
| Sorbitol | 20.0 |
| Na Saccharin | 0.2 |
| BZCl | 0.5 |
| MAG | 0.1 |
| MFP | 0.76 |
| Dicalcium phosphate dihydrate | 50.0 |
| CAB (30% A.I.) | 5.0 |
| Flavor | 1.0 |

The resultant cream exhibits a foam height of 42 and no flavor separation after 9 weeks at 120° F. This product is completely stable at 8° F. and 40° F. for a period of 9 weeks, but exhibits traces of a wet cap at 110° F. and 120° F. after 3 to 9 weeks.

EXAMPLE 14

| Ingredients | % |
| --- | --- |
| Natrosol | 1.1 |
| Na Saccharin | 0.3 |
| BZCl | 0.5 |
| MFP | 0.76 |
| Carbowax 600 | 10.0 |
| Sorbitol (70%) | 10.0 |
| H₂O deionized | 19.34 |
| Hydrated Alumina | 10.0 |
| Calcined Alumina | 42.0 |
| Flavor | 1.0 |
| CAB (30% A.I.) | 5.0 |

EXAMPLE 15

| Ingredients | % |
| --- | --- |
| Natrosol | 1.1 |
| Na Saccharin | 0.3 |
| MFP | 0.76 |
| BZCl | 0.5 |
| Carbowax 600 | 15.0 |
| Sorbitol (70%) | 5.0 |
| H₂O | 19.34 |
| Hydrated Alumina | 42.00 |
| Calcined Alumina | 10.0 |
| Flavor | 1.0 |
| CAB (30% A.I.) | 5.0 |

This product which contains 5% sorbitol, exhibits 84% soluble fluoride recovery at 12 weeks at 100° F., as compared to 61% fluoride recovery (acceptable level) for the polyethylene glycol humectant system alone under the same conditions, e.g. Examples 1 through 11. This indicates that the presence of sorbitol, in amounts as low as 5% (70% A.I.), provides superior fluoride stability.

Variations in the above formulations may be made. For example, other betaines such as lauramidopropyldimethyl betaine, cocodimethyl betaine and the like may be substituted for the cocoamidopropyldimethyl betaine in the examples. Similarly, other abrasives may be substituted for the specific abrasives in the examples.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

We claim:

1. A stable antiplaque dentifrice with improved foaming, comprising an effective amount within the range of about 0.01–5% of an antiplaque quaternary ammonium compound, at least 1.5% and up to about 2% betaine surfactant, about 20–30% of a humectant selected from the group consisting of polyethylene glycol, sorbitol, and mixtures thereof, and about 0.5–2% of a nonionic gelling agent, in an aqueous vehicle containing about 40–60% of a dental abrasive.

2. The dentifrice of claim 1, wherein the nonionic gelling agent is hydroxyethylcellulose in amounts of about 0.5–2% by weight.

3. The dentifrice according to claim 2, containing about 20–30% by weight of polyethylene glycol having a molecular weight of 600.

4. The dentifrice according to claim 2, containing about 20–30% by weight of sorbitol.

5. The dentifrice according to claim 1, containing about 40–60% by weight of a water-insoluble dental abrasive.

6. The dentifrice according to claim 3, wherein the dental abrasive is dicalcium phosphate.

7. The dentifrice according to claim 2, wherein the antiplaque agent is benzethonium chloride in an amount of about 0.01–5% by weight.

8. The dentifrice of claim 1, wherein the betaine is cocoamidopropyl betaine.

9. The dentifrice according to claim 1, which is free of nonionic and anionic surfactants.

10. The dentifrice according to claim 1, which is free of glycerin and propylene glycol.

11. The dentifrice according to claim 5, wherein the abrasive is dicalcium phosphate.

12. The dentifrice according to claim 5, wherein the abrasive is alumina.

13. The dentifrice according to claim 12, wherein the abrasive is a mixture of hydrated alumina and calcined alumina.

14. The dentifrice according to claim 2, wherein the humectant comprises about 20–30% by weight of a mixture of sorbitol and polyethylene glycol.

* * * * *